(12) United States Patent
Liu et al.

(10) Patent No.: US 12,364,879 B2
(45) Date of Patent: Jul. 22, 2025

(54) RADIOTHERAPY DEVICE, AND RADIOTHERAPY SYSTEM INCLUDING RADIOTHERAPY DEVICE AND CONTROL DRIVING DEVICE

(71) Applicant: OUR UNITED CORPORATION, Xi'an (CN)

(72) Inventors: Haifeng Liu, Xi'an (CN); Daliang Li, Xi'an (CN)

(73) Assignee: Our United Corporation, Shaanxi (CN)

( * ) Notice: Subject to any disclaimer, the term of this patent is extended or adjusted under 35 U.S.C. 154(b) by 1030 days.

(21) Appl. No.: 17/183,485

(22) Filed: Feb. 24, 2021

(65) Prior Publication Data

US 2021/0196987 A1 Jul. 1, 2021

Related U.S. Application Data

(63) Continuation of application No. PCT/CN2019/099408, filed on Aug. 6, 2019.

(30) Foreign Application Priority Data

Aug. 24, 2018 (CN) .......................... 201810974331.3

(51) Int. Cl.
 *A61N 5/10* (2006.01)
(52) U.S. Cl.
 CPC ........... *A61N 5/1084* (2013.01); *A61N 5/103* (2013.01); *A61N 5/1039* (2013.01);
 (Continued)
(58) Field of Classification Search
 CPC ........ A61N 5/10; A61N 5/103; A61N 5/1031; A61N 5/1039; A61N 5/1042;
 (Continued)

(56) References Cited

U.S. PATENT DOCUMENTS

| 5,448,611 | A | * | 9/1995 | Kerjean | ............... | A61N 5/1084 |
| | | | | | | 378/65 |
| 5,528,653 | A | * | 6/1996 | Song | .................... | A61N 5/1084 |
| | | | | | | 378/65 |

(Continued)

FOREIGN PATENT DOCUMENTS

| CN | 1481756 | 3/2004 |
| CN | 101195058 | 6/2008 |

(Continued)

OTHER PUBLICATIONS

An English translation of CN101195058A by Patent Translate. (Year: 2025).*

(Continued)

*Primary Examiner* — Allen C. Ho

(74) *Attorney, Agent, or Firm* — Patterson + Sheridan, LLP

(57) ABSTRACT

A radiotherapy device, a control driving method thereof, and a radiotherapy system are disclosed. The radiotherapy device includes a radioactive source apparatus, the radioactive source apparatus includes a source carrier and a collimator, the source carrier is provided with a plurality of radioactive sources thereon, an angle of the plurality of radioactive sources in a longitude direction is within a preset angle range; the collimator is provided with a collimating hole thereon, and radiation beams emitted from the plurality of radioactive sources intersect at a common focus after passing through the collimating hole on the collimator.

19 Claims, 12 Drawing Sheets

(52) U.S. Cl.
CPC ......... *A61N 5/1042* (2013.01); *A61N 5/1049* (2013.01); *A61N 5/1065* (2013.01); *A61N 2005/1061* (2013.01); *A61N 2005/1074* (2013.01); *A61N 2005/1094* (2013.01)

(58) Field of Classification Search
CPC .. A61N 5/1043; A61N 5/1044; A61N 5/1048; A61N 5/1049; A61N 2005/1061; A61N 5/1064; A61N 5/1065; A61N 5/1067; A61N 2005/1074; A61N 5/1077; A61N 5/1078; A61N 5/1084; A61N 2005/1094; A61N 2005/1052
USPC .......................................................... 378/65
See application file for complete search history.

(56) References Cited

U.S. PATENT DOCUMENTS

| | | | | |
|---|---|---|---|---|
| 5,537,452 | A * | 7/1996 | Shepherd | A61N 5/1084 378/65 |
| 5,757,886 | A * | 5/1998 | Song | A61N 5/1084 378/150 |
| 6,044,126 | A * | 3/2000 | Rousseau | A61N 5/1031 378/65 |
| 6,438,203 | B1 * | 8/2002 | Shipeng | A61N 5/1084 378/65 |
| 6,512,813 | B1 * | 1/2003 | Krispel | G21K 1/04 378/65 |
| 6,931,096 | B2 * | 8/2005 | Carlsson | A61N 5/1084 378/65 |
| 6,968,036 | B2 * | 11/2005 | Carlsson | G21K 1/04 378/65 |
| 6,977,987 | B2 * | 12/2005 | Yamashita | A61N 5/10 378/65 |
| 7,188,999 | B2 * | 3/2007 | Mihara | A61N 5/1082 378/197 |
| 7,239,684 | B2 * | 7/2007 | Hara | A61N 5/1049 378/65 |
| 7,283,610 | B2 * | 10/2007 | Low | A61N 5/1027 378/65 |
| 7,656,999 | B2 * | 2/2010 | Hui | A61N 5/1084 378/65 |
| 7,664,226 | B2 * | 2/2010 | Hui | A61B 6/06 378/65 |
| 7,672,429 | B2 * | 3/2010 | Urano | A61N 5/1049 378/65 |
| 8,094,785 | B2 * | 1/2012 | Heid | G21K 1/04 378/150 |
| 8,938,047 | B2 * | 1/2015 | Nordström | A61N 5/1078 378/65 |
| 8,965,096 | B2 * | 2/2015 | Yamada | A61B 6/5288 378/62 |
| 9,358,404 | B2 * | 6/2016 | Danielsson | A61N 5/103 |
| 9,433,802 | B2 * | 9/2016 | Handa | A61N 5/1049 |
| 9,526,917 | B2 * | 12/2016 | Carlsson | A61N 5/1081 |
| 9,526,919 | B2 * | 12/2016 | Liu | A61N 5/1039 |
| 9,616,251 | B2 * | 4/2017 | Filiberti | A61N 5/10 |
| 9,974,496 | B2 * | 5/2018 | Liu | A61N 5/1049 |
| 9,974,977 | B2 * | 5/2018 | Lachaine | A61B 8/085 |
| 9,974,980 | B2 * | 5/2018 | Liu | A61N 5/1081 |
| 10,124,190 | B2 * | 11/2018 | Ojha | A61B 5/0035 |
| 10,166,407 | B2 * | 1/2019 | Stahl | A61B 6/563 |
| 10,441,816 | B2 * | 10/2019 | Liu | A61B 6/4435 |
| 10,463,882 | B2 * | 11/2019 | Liu | A61B 6/035 |
| 10,478,138 | B2 * | 11/2019 | Tian | A61B 6/032 |
| 10,653,896 | B2 * | 5/2020 | Xiao | A61N 5/1081 |
| 10,716,952 | B2 * | 7/2020 | Liu | A61N 5/01 |
| 10,720,255 | B2 * | 7/2020 | Zheng | A61N 5/1084 |
| 10,744,343 | B2 * | 8/2020 | Sjölund | A61N 5/1031 |
| 10,806,949 | B2 * | 10/2020 | Li | A61N 5/1082 |
| 10,850,123 | B2 * | 12/2020 | Liu | A61N 5/1031 |
| 10,857,385 | B2 * | 12/2020 | Xiao | A61N 5/1045 |
| 10,888,711 | B2 * | 1/2021 | Nordström | A61N 5/1031 |
| 10,953,243 | B2 * | 3/2021 | Liu | A61N 5/1049 |
| 10,953,244 | B2 * | 3/2021 | Liu | A61N 5/1042 |
| 10,974,072 | B2 * | 4/2021 | Liu | A61N 5/1044 |
| 11,058,892 | B2 * | 7/2021 | Wilbur | G21K 1/025 |
| 11,135,450 | B2 * | 10/2021 | Yan | A61N 5/1067 |
| 11,291,857 | B2 * | 4/2022 | Riad | A61N 5/1031 |
| 11,324,972 | B2 * | 5/2022 | Liu | A61N 5/06 |
| 11,331,516 | B2 * | 5/2022 | Liu | A61N 5/103 |
| 11,351,396 | B2 * | 6/2022 | Nordström | A61N 5/1084 |
| 11,458,331 | B2 * | 10/2022 | Sjölund | A61N 5/1045 |
| 11,464,999 | B2 * | 10/2022 | Liu | A61N 5/1042 |
| 11,602,647 | B2 * | 3/2023 | Gou | A61N 5/1069 |
| 11,684,803 | B2 * | 6/2023 | Li | A61N 5/1049 378/65 |
| 11,759,654 | B2 * | 9/2023 | Liu | A61N 5/1067 378/65 |
| 12,109,438 | B2 * | 10/2024 | Li | A61N 5/1084 |
| 12,115,390 | B2 * | 10/2024 | Liu | A61N 5/1042 |
| 2009/0121155 | A1 | 5/2009 | Brown et al. | |

FOREIGN PATENT DOCUMENTS

| | | |
|---|---|---|
| CN | 203694431 | 7/2014 |
| CN | 104001269 A | 8/2014 |
| CN | 104837523 | 8/2015 |
| CN | 109011217 | 12/2018 |
| CN | 209714022 U | 12/2019 |
| WO | 2015096498 A1 | 7/2015 |

OTHER PUBLICATIONS

China Application No: 201810974331.3, First Office Action, dated Mar. 15, 2023.

* cited by examiner

US 12,364,879 B2

RADIOTHERAPY DEVICE, AND RADIOTHERAPY SYSTEM INCLUDING RADIOTHERAPY DEVICE AND CONTROL DRIVING DEVICE

CROSS-REFERENCE TO RELATED APPLICATIONS

The present disclosure is a continuation application in the U.S. for the PCT application No. PCT/CN2019/099408 filed on Aug. 6, 2019, entitled "RADIOTHERAPY APPARATUS AND SYSTEM, AND CONTROL DRIVING METHOD AND APPARATUS", which claims priority to Chinese Patent Application No. 201810974331.3 filed on Aug. 24, 2018, entitled "RADIOTHERAPY SYSTEM AND CONTROL DRIVING METHOD THEREOF", the entire contents of which are incorporated herein by reference.

TECHNICAL FIELD

The present disclosure relates to the field of medical technologies, and in particular to, a radiotherapy device, a control driving method thereof, and a radiotherapy system.

BACKGROUND

With the development of medical technologies, radiotherapy devices are increasingly widely used in the treatment of tumors.

A radiotherapy device configured to treat a head tumor in the related art mainly includes a head gamma knife, which emits Y-rays using a natural isotope, e.g., a radioactive source cobalt-60, and kills tumor cells using the radioactivity of the rays. However, since rays will also damage normal tissues or cells, an existing head gamma knife generally includes 30 or 180 radioactive sources, a plurality of radioactive sources emits radiation beams from different directions, and the radiation beams focus on a common focus. There is a highest radiation dose rate at the common focus, and radiation beams emitted from each of the radioactive sources cause less damage to the normal tissues or cells. During tumor treatment, the common focus may be irradiated on the tumor, so as to kill the tumor cells whilst protecting the normal tissues or cells to achieve the tumor treatment effects.

SUMMARY

The present disclosure provides a radiotherapy device, a radiotherapy system. a control driving method, and a control driving device. The technical solutions are as follows:

In one aspect, a radiotherapy device is provided, including a radioactive source apparatus. The radioactive source apparatus includes a source carrier and a collimator, the source carrier is provided with a plurality of radioactive sources thereon, an angle of the plurality of radioactive sources in a longitude direction is within a preset angle range; the collimator is provided with a collimating hole thereon, and radiation beams emitted from the plurality of radioactive sources intersect at a common focus after passing through the collimating hole on the collimator.

In another aspect, a control driving method for a radiotherapy device is provided. The radiotherapy device is any one of the radiotherapy devices provided in the present disclosure. The method includes: acquiring at least one beam emission angle range; and driving the radiotherapy device to emit radiation beams in the beam emission angle range, the radiation beams intersecting at a common focus.

In still another aspect, a control driving device for a radiotherapy device is provided, including: a processor configured to implement any one of the control driving methods provided in the present disclosure.

In yet still another aspect, a radiotherapy system is provided, including: any one of the radiotherapy devices provided in the present disclosure, and the control driving device provided in the present disclosure.

DETAILED DESCRIPTION

In order to make the objectives, technical solutions, and advantages of the present disclosure clearer, embodiments of the present disclosure will be further described in detail below with reference to the accompanying drawings.

Figure 1:
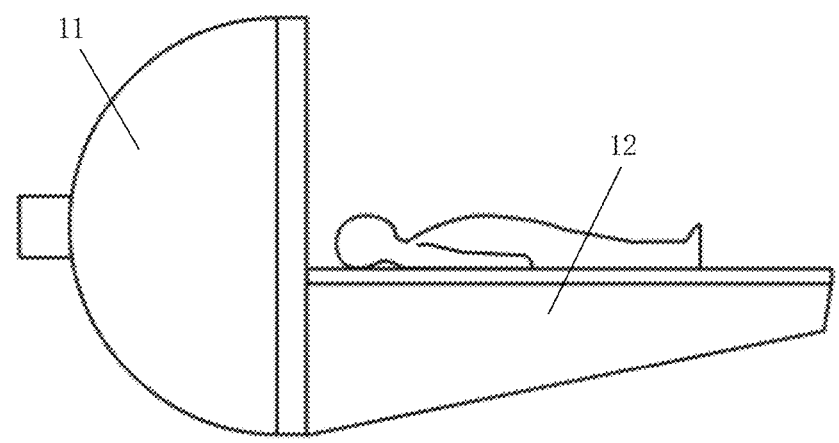
FIG. 1 is a schematic structural diagram of an existing radiotherapy device provided in an embodiment of the present disclosure.
Figure 2:
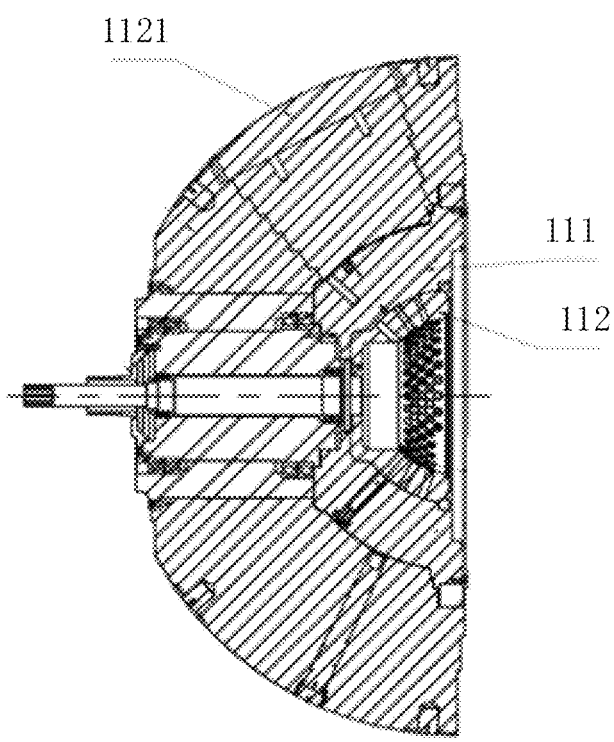
FIG. 2 is a schematic structural diagram of an existing radioactive source apparatus provided in an embodiment of the present disclosure.

A structure of an existing radiotherapy device usable for a head tumor is shown in FIG. 1 and FIG. 2. A source carrier 111 is equipped with a plurality of radioactive sources, and radiation beams emitted from the plurality of radioactive sources intersect at a common focus after passing through a collimating hole on a collimator 112. The common focus is located within a cavity of a radioactive source apparatus 11 of the radiotherapy device. A treatment couch 12 is configured to carry a patient and move the patient to the inside of a treatment chamber of the radioactive source apparatus 11, such that a nidus of the patient is located at the common focus for radiotherapy.

Figure 3:
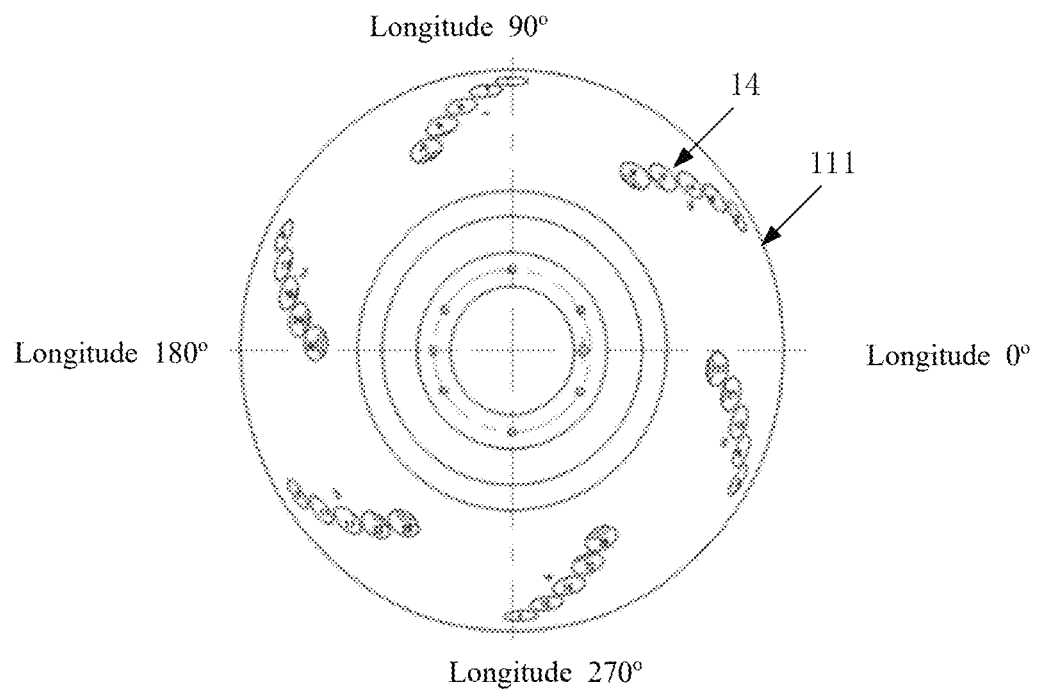
FIG. 3 is a schematic structural diagram of a top view of an existing source carrier provided in an embodiment of the present disclosure.
Figure 4:
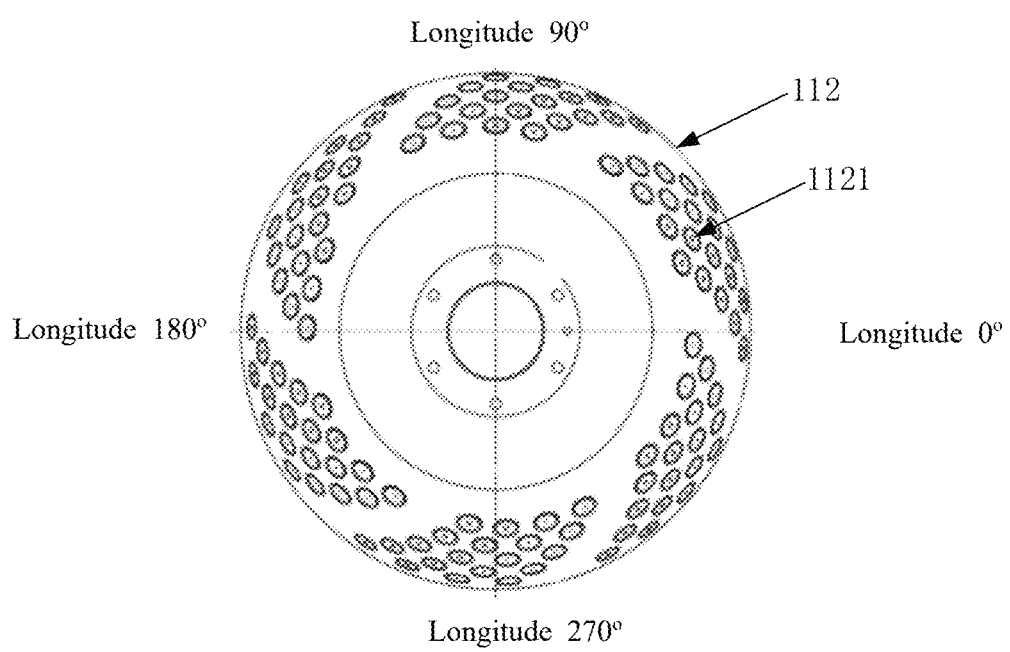
FIG. 4 is a schematic structural diagram of a top view of an existing collimator provided in an embodiment of the present disclosure.

The source carrier 111 of the existing radiotherapy device is bowl-shaped as shown in FIG. 3. Radioactive sources 14 are divided into six groups, each group of which includes five radioactive sources 14, i.e., the source carrier 111 is equipped with 30 radioactive sources 14 in total that are distributed on the source carrier 111. A structure of the collimator 112 is shown in FIG. 4. Six collimating channel groups are provided on the collimator 112, and the six collimating channel groups correspond to positions of the six groups of radioactive sources 14. Each collimating channel group includes four subgroups, where collimating holes 1121 in one of the subgroups are filled with solid tungsten rods to realize closed source shielding, each of the other subgroups includes 5 collimating holes, and the collimating holes in different subgroups are of different sizes.

During treatment, the source carrier 111 and the collimator 112 may be driven to rotate mutually, to switch between different sizes of the collimating holes 1121 and realize switching on/off the radioactive sources 14 by shielding the radioactive sources 14 through the collimator 112. However, the switching between different sizes of the collimating holes 1121 in the six groups and the switching on/off the radioactive sources 14 are implemented simultaneously, and one group thereof cannot be controlled individually. Therefore, during the treatment, sensitive tissues and organs can be avoided only by adjusting a gamma angle. For example, during treatment of the head tumor, if it is necessary to avoid the sensitive tissues and organs, e.g., eyes and other important nerves, the existing radiotherapy device can avoid irradiation of the sensitive tissues and organs only by adjusting a gamma angle of the patient, i.e., by adjusting a pitch angle of head.

Figure 5:
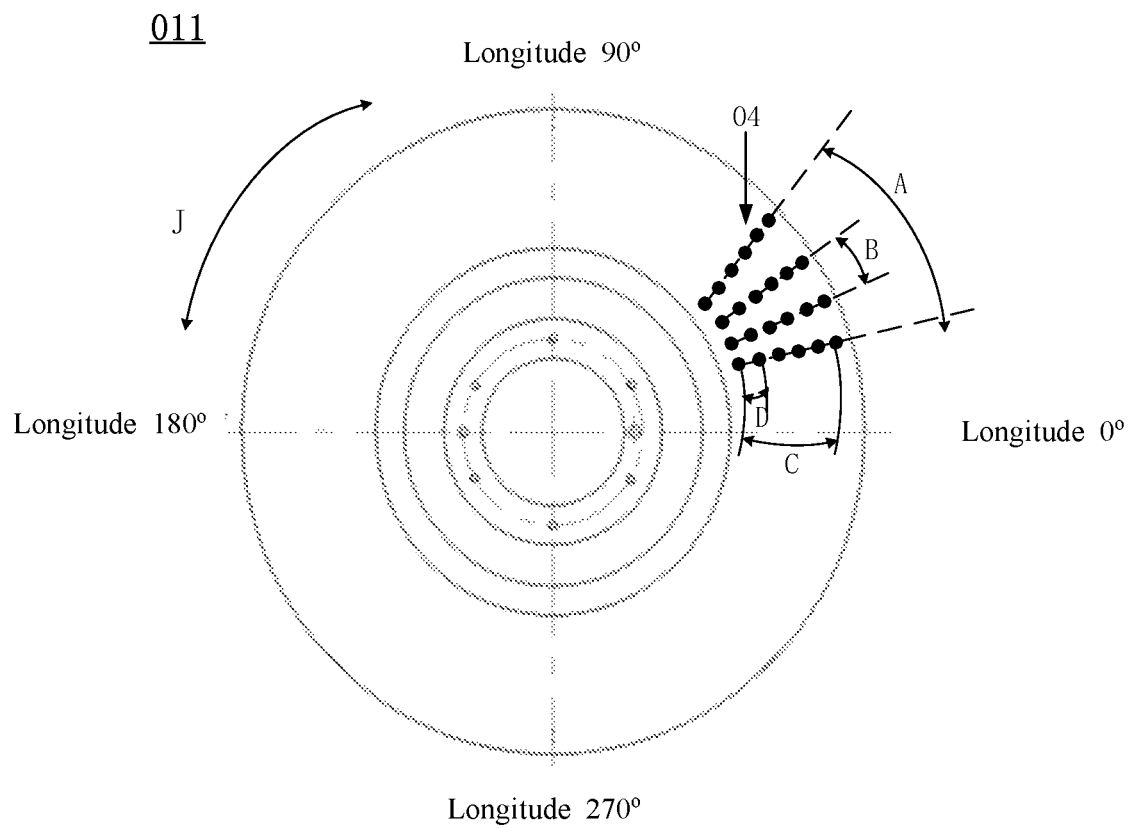
FIG. 5 is a schematic diagram of a source carrier provided in an embodiment of the present disclosure.
Figure 6:
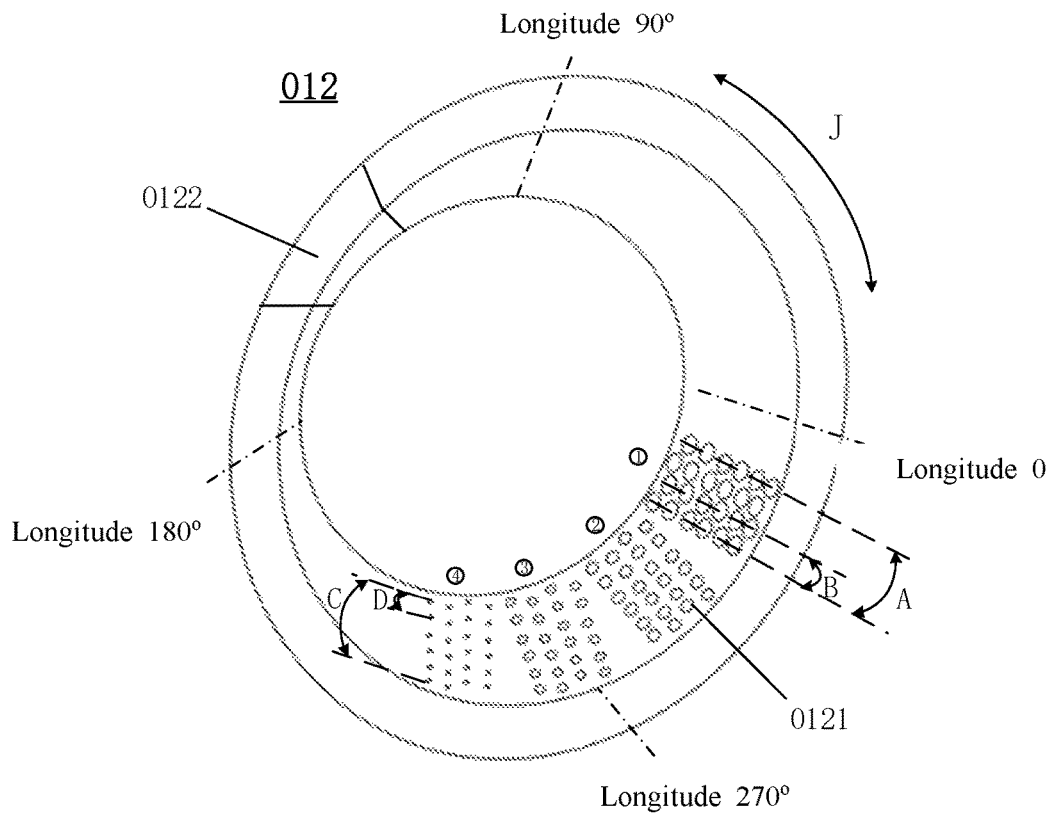
FIG. 6 is a schematic diagram of a collimator provided in an embodiment of the present disclosure.
Figure 7:
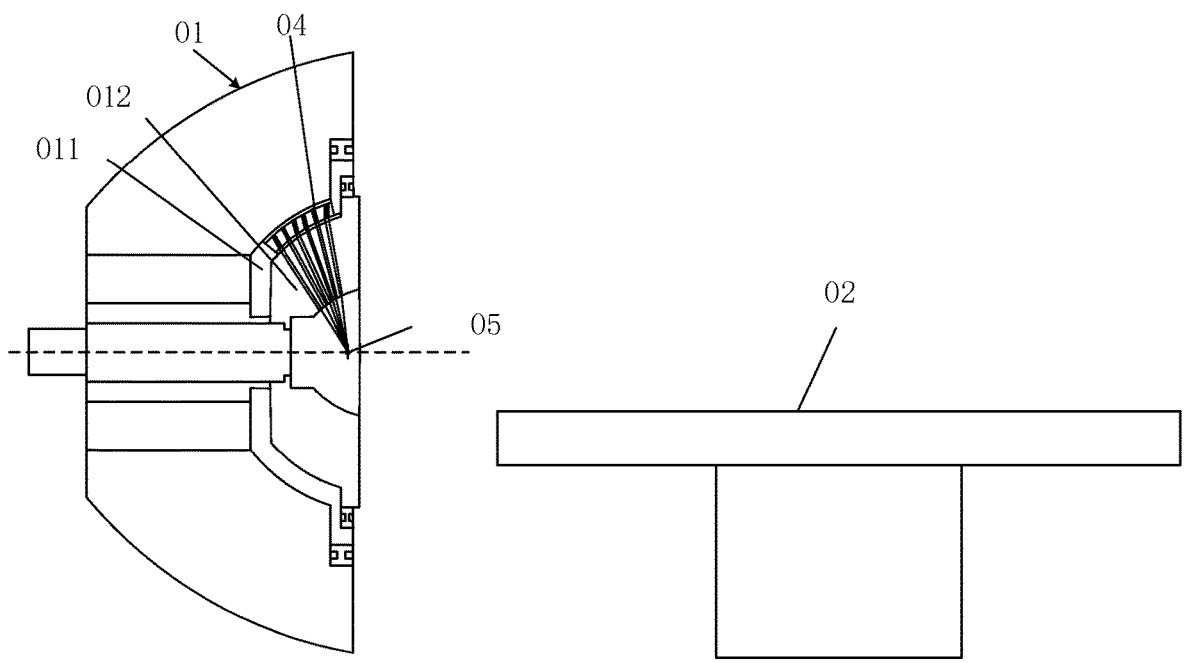
FIG. 7 is a schematic diagram of a radiotherapy device provided in an embodiment of the present disclosure.

A radiotherapy device provided in the present disclosure, as shown in FIG. 5 to FIG. 7, includes a radioactive source apparatus 01. The radioactive source apparatus 01 includes a source carrier 011 and a collimator 012. As shown in FIG. 5, the source carrier 011 is provided with a plurality of radioactive sources 04 thereon, and an angle of the plurality of radioactive sources 04 in a longitude direction is within a preset angle range. As shown in FIG. 6, the collimator 012 is provided with a plurality of collimating hole groups, an angle of each of the collimating hole groups in the longitude direction is within the preset angle range, each of the collimating hole groups includes a plurality of collimating holes 0121, and radiation beams emitted from the plurality of radioactive sources 04 intersect at a common focus 05 as shown in FIG. 7 after passing through the collimating holes 0121 of the collimating hole groups.

Figure 8:
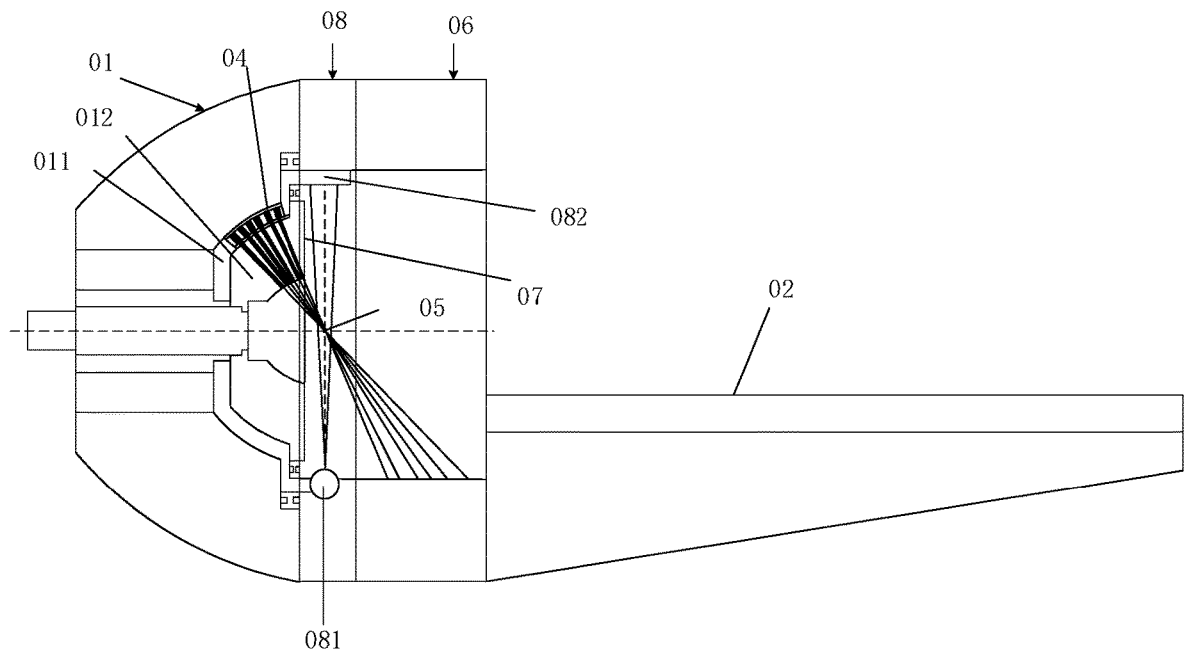
FIG. 8 is a schematic diagram of another radiotherapy device provided in an embodiment of the present disclosure.
Figure 9:
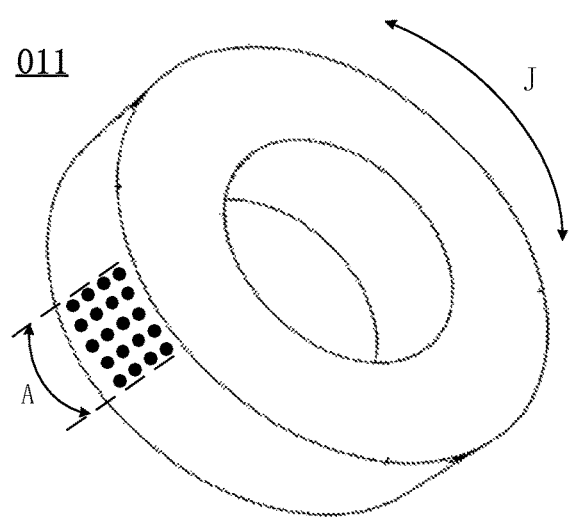
FIG. 9 is a schematic diagram of another source carrier provided in an embodiment of the present disclosure.
Figure 10:
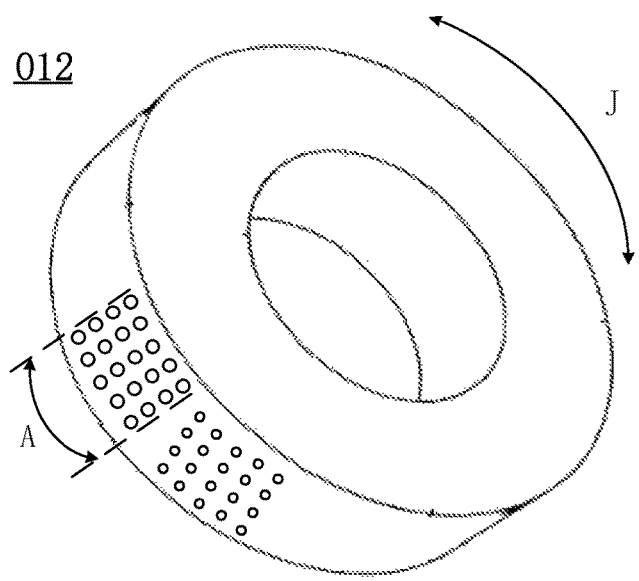
FIG. 10 is a schematic diagram of another collimator provided in an embodiment of the present disclosure.
Figure 11:
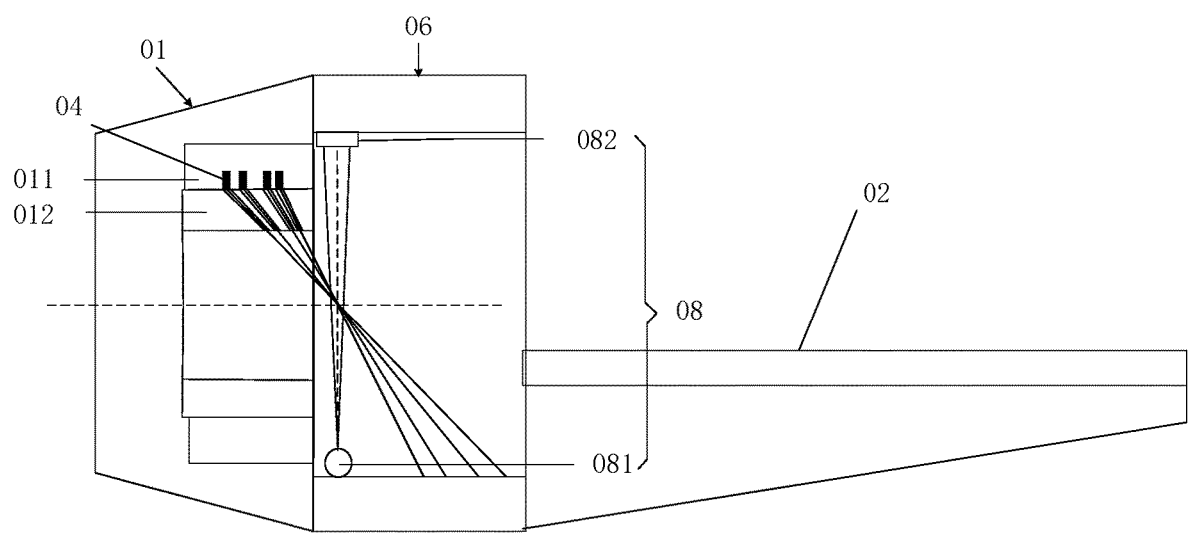
FIG. 11 is a schematic diagram of still another radiotherapy device provided in an embodiment of the present disclosure.
Figure 12:
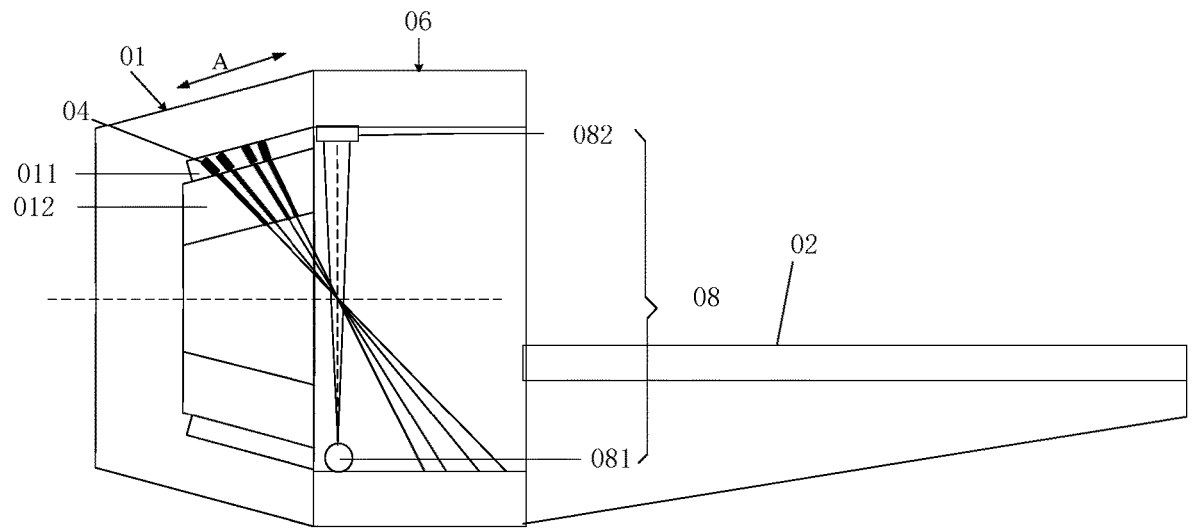
FIG. 12 is a schematic diagram of yet still another radiotherapy device provided in an embodiment of the present disclosure.

In the present disclosure, for example, as shown in FIG. 7 and FIG. 8, the radioactive source apparatus 01 may be bowl-shaped, the source carrier 011 thereof may be as shown in FIG. 5, and the source carrier 011 is bowl-shaped. The collimator 012 may be as shown in FIG. 6. The collimator 012 is bowl-shaped, and a longitude direction thereof is as shown by an arrow J in the figure, which is a trend direction of longitude 0°-360°. Alternatively, as shown in FIG. 11, the radioactive source apparatus 01 may also be cylindrical, the source carrier 011 thereof may be as shown in FIG. 9, and the collimator 012 may be as shown in FIG. 10. Both the source carrier 011 and the collimator 012 are cylindrical, and a longitude direction thereof is as shown by the arrow J in the figure, which is the trend direction of longitude 0° to 360°. In FIG. 11, both ends of the source carrier 011 are of a same size, and of course, may also be of different sizes, an example of which is shown in FIG. 12. A specific shape of the radioactive source apparatus 01 is not limited in the present disclosure, and the above description is only taken as an example.

The angle range in the present disclosure is described below with the radiotherapy device shown in FIG. 7 and FIG. 8 as an example. As shown in FIG. 5, an angle of a radioactive source 04 in the longitude direction is an angle formed with reference to a center of the radioactive source 04. It should be particularly noted here that if the radioactive source 04 includes a row, and centers of a plurality of radioactive sources 04 located in a same row are on a same longitude line, then an angle of the plurality of radioactive sources 04 in the longitude direction is considered to be zero degree. In the present disclosure, the preset angle range is greater than or equal to zero degree. As shown in FIG. 6, an angle of the collimator 012 in the longitude direction is an angle formed with reference to a center of the collimator 012. It should be particularly noted here that if the collimating hole 0121 includes a row, and centers of a plurality of collimating holes 0121 located in a same row are on a same longitude line, then an angle of the plurality of collimating holes 0121 in the longitude direction is considered to be zero degree. In the present disclosure, the preset angle range is greater than or equal to zero degree.

FIG. 5 shows a source carrier 011 provided in the present disclosure. The source carrier 011 is provided with a plurality of radioactive sources 04, and an angle of the plurality of radioactive sources 04 in the longitude direction is A. For example, a range of the angle A may be 15 degrees to 60 degrees, i.e., 15 degrees≤A≤60 degrees, and the angle A may be any angle within the range of 15 degrees to 60 degrees. For example, the range of the angle A may be 5 degrees to 60 degrees, i.e., 5 degrees≤A≤60 degrees, i.e., the angle A may be any angle within the range of 5 degrees to 60 degrees. For example, the angle A may be 5 degrees, 8 degrees, 10 degrees, 12 degrees, 18 degrees, 20 degrees, 25 degrees, 30 degrees, 40 degrees, 45 degrees, 50 degrees, or 60 degrees. The number and arrangement of the radioactive sources 04 are not limited in the present disclosure, and the corresponding number of radioactive sources 04 may generally be 20 to 180, e.g., 30 or 180. In the present disclosure, an example description is provided with 24 radioactive sources 04 shown in FIG. 5 as an example.

For example, FIG. 6 shows a bowl-shaped collimator 012 provided in the present disclosure. FIG. 6 takes the collimator 012 provided with 4 collimating hole groups as an example, namely a collimating hole group No. ①, a collimating hole group No. ②, a collimating hole group No. ③, and a collimating hole group No. ④. Each of the collimating hole groups includes 24 collimating holes 0121, and corresponds to the distribution of the radioactive sources 04. With the collimating hole group No. ① as an example, radiation beams emitted from the plurality of radioactive sources 04 intersect at a common focus after passing through the collimating holes 0121 of the collimating hole group No. ①. An angle of the collimating hole group No. ①, an angle of the collimating hole group No. ②, an angle of the collimating hole group No. 3, and an angle of the collimating hole group No. ④ in the longitude direction are within the preset angle range. FIG. 6 takes the collimating hole group No. ① as an example. The angle of the collimating hole group No. ① in the longitude direction (a direction indicated by an arrow J in FIG. 6) is A. For example, the angle A is the same as a preset angle of the radioactive source 04 of the source carrier 011, either of which is 5 degrees to 60 degrees.

The collimator 012 is provided with a plurality of collimating hole groups, and the collimator 012 may be provided with two or more than two collimating hole groups. FIG. 6 only provides an example description with the collimator 012 provided with 4 collimating hole groups as an example. Each of the collimating hole groups includes a plurality of collimating holes 0121, and the number and arrangement of the radioactive sources 04 corresponding to the plurality of collimating holes 0121 correspond to the plurality of radioactive sources 04 on the source carrier 011, such that the radiation beams emitted from the radioactive sources 04 intersect at a common focus after passing through the collimating holes 0121.

For example, as shown in FIG. 11, the radioactive source apparatus 01 may also be cylindrical. Then, as shown in FIG. 9, the source carrier 011 may also be cylindrical as shown in FIG. 9, and its longitude direction is a direction indicated by an arrow J in FIG. 9. In FIG. 9, both ends of the cylindrical source carrier 011 are of a same size. The specific number and arrangement of the radioactive sources 04 are not limited in the present disclosure. FIG. 9 only provides an example description with 20 radioactive sources 04 as an example. The collimator 012 may also be cylindrical as shown in FIG. 10, and the plurality of collimating holes corresponds to the number and arrangement of the radioactive sources 04. The description will not be repeated here. The number of collimating hole groups on the collimator 012 is not limited in the present disclosure. FIG. 10 provides an example description with the collimator 012 provided with two collimating hole groups as an example and with each of the collimating hole groups including 20 collimating holes as an example.

Of course, the radioactive source apparatus 01 may also be as shown in FIG. 12, and the radioactive source apparatus 01 may also be cylindrical. In FIG. 12, a cylindrical source carrier 011 with both ends of different sizes is taken as an example.

The present disclosure provides a radiotherapy device. The source carrier 011 of the radiotherapy device is provided with a plurality of radioactive sources 04, and an angle of the radioactive sources 04 in a longitude direction is within a preset angle range. The plurality of radioactive sources 04 on the source carrier 011 is distributed within the preset angle range of the longitude direction. The radiotherapy device may drive the plurality of radioactive sources 04 through the source carrier 011 to rotate along a center axis of the radiotherapy device, switch off the radioactive sources 04 when passing through sensitive tissues or organs; and switch on the radioactive sources 04 when irradiating normal tissues and organs, thereby protecting the sensitive tissues and organs, e.g., eyes, from additional damages during the treatment of a head tumor.

As shown in FIG. 5, a specific example description of the source carrier 011 provided in the present disclosure will be provided below.

For example, for the source carrier 011 provided in the present disclosure, the plurality of radioactive sources 04 in the longitude direction is divided into a plurality of groups, and an angle range of two adjacent groups of radioactive sources 04 is 2 degrees to 15 degrees. For example, among the plurality of radioactive sources 04, an angle of any two adjacent groups of radioactive sources 04 is identical, or an angle of two different adjacent groups of radioactive sources 04 is different. This is not limited in the present disclosure. FIG. 5 only shows an example description. As shown in FIG. 5, the plurality of radioactive sources 04 is divided into 5 groups. With an angle B of two adjacent groups of radioactive sources 04 (FIG. 5 takes two schematic groups as an example) as an example, the angle B may be 2 degrees to 15 degrees, i.e., 2 degrees≤B≤15 degrees, and the angle B may be any angle within the range of 2 degrees to 15 degrees. For example, the angle B may be 2 degrees, 2.5 degrees, 3 degrees, 5 degrees, 6 degrees, 8 degrees, 10 degrees, 12 degrees, or 15 degrees.

For the source carrier 011 provided in the present disclosure, an angle range of the plurality of radioactive sources 04 in a latitude direction is 20 degrees to 60 degrees. For example, as shown in FIG. 5, a plurality of radioactive sources 04 is provided within an angle C of the source carrier 011 in the longitude direction. For example, the angle C may be 20 degrees to 60 degrees, i.e., 20 degrees≤C≤60 degrees, and the angle C may be any angle within the range of 20 degrees to 60 degrees. For example, the angle C may be 20 degrees, 25 degrees, 30 degrees, 38 degrees, 40 degrees, 45 degrees, 50 degrees, 53 degrees, or 60 degrees.

For example, for the source carrier 011 provided in the present disclosure, an angle range of any two adjacent radioactive sources 04 is 1 degree to 10 degrees in the latitude direction. For example, among the plurality of radioactive sources 04, an angle of any two adjacent groups of radioactive sources 04 is identical in the latitude direction, or an angle of any two adjacent groups of radioactive sources 04 is different in the latitude direction. This is not limited in the present disclosure. FIG. 5 only shows an example description. For example, as shown in FIG. 5, with two of the radioactive sources 04 as an example, an angle of the two radioactive sources 04 is D in the latitude direction, the angle D may be 1 degree to 10 degrees, i.e., 1 degrees≤D≤10 degrees, and the angle D may be any angle within the range of 1 degree to 10 degrees. For example, the angle D may be 1 degree, 2 degrees, 3 degrees, 5 degrees, 6 degrees, 8 degrees, 9 degrees, or 10 degrees.

An example of the source carrier 011 shown in FIG. 5 is that the radioactive sources 04 include a plurality of rows in the longitude direction and a plurality of rows in the latitude direction, the radioactive sources 04 in a same longitudinal row have the same longitude, and the radioactive sources 04 in a same latitudinal row have the same latitude. Further, in order to achieve non-coplanar irradiation and better protect normal tissues, for the source carrier 011 provided in the present disclosure, the radioactive sources 04 have different positions in the latitude direction. That is, each of the radioactive sources 04 has a different latitude.

For the source carrier 011 provided in the present disclosure, the source carrier 011 is provided with a plurality of radioactive source holes, and the radioactive sources 04 are immovably installed within the radioactive source holes. Alternatively, the source carrier 011 is provided with a source box position matching a shape of a source box, the source box may be immovably installed at the source box position, and the source box is provided with a plurality of radioactive sources 04. For example, the source box position may be a through hole or a blind hole, and a plurality of collimating holes is provided on the source carrier 011, such that radiation beams emitted from the radioactive sources 04 may be emitted through the collimating holes. Shapes and structures of the source box and the source box position are not limited in the present disclosure.

The source carrier 011 is further provided with a source box connecting part configured to fix the source box at the source box position. Similarly, the source box is also provided with a connecting part for connection to the source box position. For example, the source carrier 011 and the source box may be connected by a screw or a clip. The connection and fixing approaches of the source box and the source box position are not limited in the present disclosure. Only an example description is provided with the above description as an example.

For the source carrier 011 provided in the present disclosure, the source box is further provided with a connecting part configured to replace the source box. For example, the source box connecting part may be a screw hole, which may be screwed to a source guide rod. Alternatively, the source box connecting part and the source guide rod may be connected by magnetic adsorption. The connection between the source box and the source guide rod and the approach of replacing the source box are not limited in the present disclosure. Only an example description is provided with the above description as an example.

For the source carrier 011 provided in the present disclosure, the source box and the source carrier 011 may be made of different materials. For example, the source box may be formed of a tungsten alloy, and the source carrier 011 may be formed of cast iron.

As shown in FIG. 6, a specific example description of the collimator 012 provided in the present disclosure will be provided below.

For the collimator 012 provided in the present disclosure, a space between two adjacent collimating holes is greater than a size of the radioactive source 04 in the longitude direction. Therefore, the collimator 012 may be misaligned with the radioactive source 04 only by a small angle, such that the radioactive source 04 is shielded by the space between the collimating holes, to avoid the use of shielding sites 0122 for shielding. Only a small angle is required for misalignment, thus realizing fast switching on/off the source.

For example, for the collimator 012 provided in the present disclosure, each collimating hole group includes a plurality of rows in the longitude direction, and an angle range of two adjacent rows of radioactive sources 04 is 2 degrees to 15 degrees. For example, among the collimating hole groups, an angle of any two adjacent rows is identical, or an angle of two different adjacent rows is different. This is not limited in the present disclosure. FIG. 6 only shows an example description. As shown in FIG. 6, the plurality of radioactive sources 04 is divided into 4 rows. With an angle B of two adjacent rows of collimating holes (FIG. 6 takes two schematic rows as an example) as an example, the angle B may range from 2 degrees to 15 degrees, i.e., 2 degrees≤B≤15 degrees, and the angle B may be any angle within the range of 2 degrees to 15 degrees. For example, the angle B may be 2 degrees, 2.5 degrees, 3 degrees, 5 degrees, 6 degrees, 8 degrees, 10 degrees, 12 degrees, or 15 degrees.

For the collimator 012 provided in the present disclosure, an angle range of the collimating hole group in the latitude direction is 20 degrees to 60 degrees. For example, as show in FIG. 6, the angle C may range from 20 degrees to 60 degrees, i.e., 20 degrees≤C≤60 degrees, and the angle C may be any angle within the range of 20 degrees to 60 degrees. For example, the angle C may be 20 degrees, 25 degrees, 30 degrees, 38 degrees, 40 degrees, 45 degrees, 50 degrees, 53 degrees, or 60 degrees.

For example, for the collimator 012 provided in the present disclosure, an angle range of any two adjacent collimating holes is 1 degree to 10 degrees in the latitude direction. For example, an angle of any two adjacent collimating holes is identical in the latitude direction, or an angle of any two adjacent collimating holes is different in the latitude direction. This is not limited in the present disclosure. FIG. 6 only shows an example description. For example, as shown in FIG. 6, with two of the collimating holes as an example, an angle of the two collimating holes is D in the latitude direction, the angle D may range from 1 degree to 10 degrees, i.e., 1 degree D≤10 degrees, and the angle D may be any angle within the range of 1 degree to 10 degrees. For example, the angle D may be 1 degree, 2 degrees, 3 degrees, 5 degrees, 6 degrees, 8 degrees, 9 degrees, or 10 degrees.

An example of the collimator 012 shown in FIG. 6 is that the collimating holes 0121 of the collimating hole group include a plurality of rows in the longitude direction and a plurality of rows in the latitude direction, the radioactive sources 04 in a same longitudinal row have the same longitude, and the radioactive sources 04 in a same latitudinal row have the same latitude. Further, in order to achieve non-coplanar irradiation and better protect normal tissues, for the source carrier 011 provided in the present disclosure, the collimating holes 0121 have different positions in the latitude direction. That is, each of the collimating holes 0121 has a different latitude.

For the collimator 012 provided in the present disclosure, the collimator 012 further includes the shielding sites 0122 configured to shield the radiation beams from the plurality of radioactive sources 04, i.e., rays from the radioactive sources 04 may be shielded through the collimator 012, to realize switching off the source. Specific positions of the shielding sites 0122 on the collimator 012 are not limited in the present disclosure. FIG. 6 provides an example description with the positions of the shielding sites 0122 opposite to the positions of the collimating hole groups as an example.

For example, for the collimator 012 provided in the present disclosure, the shielding sites 0122 are located between any two adjacent collimating hole groups among the plurality of collimating hole groups. For example, as shown in FIG. 13, an example description is provided with the shielding sites 0122 located between the collimating hole group No. ② and the collimating hole group No. ③ as an example.

Figure 13:
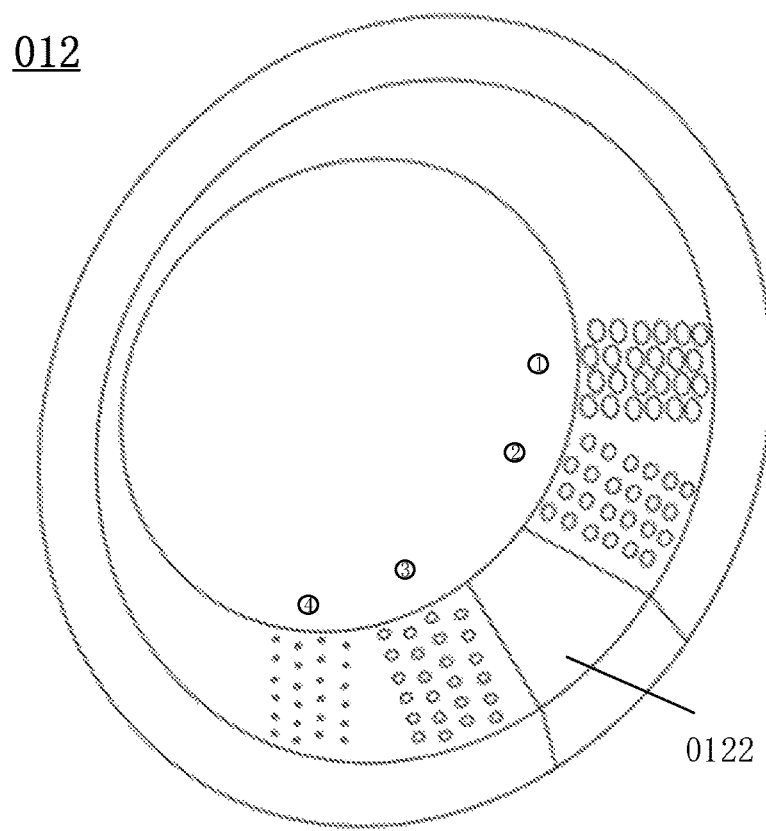
FIG. 13 is a schematic diagram of still another collimator provided in an embodiment of the present disclosure.

An example in FIG. 13 is that only one shielding site 0122 is included. For the collimator 012 provided in the present disclosure, the collimator 012 includes a plurality of shielding sites 0122. For example, the shielding sites 0122 may also be provided between the collimating hole group No. ① and the collimating hole group No. ②. The shielding sites 0122 may also be provided between the collimating hole group No. ③ and the collimating hole group No. ④. The shielding sites 0122 may also be provided between two adjacent collimating hole groups. The number and distribution of the plurality of shielding sites 0122 are not limited in the present disclosure. Only an example description is provided with the above description as an example.

For the collimator 012 provided in the present disclosure, the collimator 012 includes an inner collimator and an outer collimator that are immovably connected, and collimating holes on the inner collimator and collimating holes on the outer collimator are arranged correspondingly. That is, the collimator 012 may include double layers, and the inner collimator and the outer collimator may be connected and fixed by screws.

For the collimator 012 provided in the present disclosure, the collimator 012 includes an inner collimator and an outer collimator that are rotatable relatively. For example, if an accident occurs during treatment, the source may be fast switched off through the inner collimator, then the shielding sites 0122 may be aligned with the radioactive sources 04 by rotating the outer collimator to shield the radioactive sources 04, and then the shielding sites 0122 of the inner collimator may be further aligned with the radioactive sources 04 to achieve completely switching off the source.

For the collimator 012 provided in the present disclosure, the collimating holes on the inner collimator are taper holes, and/or the collimating holes on the outer collimator are straight holes. For example, the collimating holes on the inner collimator may be straight holes, and the collimating holes on the outer collimator may also be straight holes; or the collimating holes on the inner collimator may be taper holes, while the collimating holes on the outer collimator may be straight holes; or the collimating holes on the inner collimator and the collimating holes on the outer collimator may all be taper holes.

The collimator 012 provided in the present disclosure is provided with a shielding body at the shielding site 0122, and a material density of the shielding body is greater than a material density of the collimator 012. For example, the shielding body is immovably connected to the collimator 012, and the shielding body may be made of a tungsten block or a lead block or an alloy thereof. The collimator 012 may be made of cast iron. Therefore, the shielding body can achieve better shielding of the radioactive sources 04.

A radiotherapy device provided in the present disclosure includes the radioactive source apparatus 01. The radioactive source apparatus 01 includes the source carrier 011 and the collimator 012, the source carrier 011 is provided with a plurality of radioactive sources 04 thereon, an angle of the plurality of radioactive sources 04 in a longitude direction is within a preset angle range; the collimator 012 is provided with a collimating hole 0121 thereon, and radiation beams emitted from the plurality of radioactive sources 04 intersect at a common focus after passing through the collimating hole 0121 on the collimator 012. Since the plurality of radioactive sources 04 is distributed within the preset angle range of the longitude direction, the plurality of radioactive sources 04 may be driven through the source carrier 011 to rotate along the center axis of the radiotherapy device, thereby switching off the radioactive sources 04 when passing through sensitive tissues or organs; and switching on the radioactive sources 04 when irradiating normal tissues and organs, thereby protecting the sensitive tissues and organs, e.g., eyes, from additional damages during the treatment of a head tumor.

Regarding the description of the source carrier 011 and the collimator 012, the above description is only taken as an example. The arrangement of the source carrier 011 and the collimator 012 may also be used in a rotation axis of a cylindrical radioactive source. This will not be repeated here.

Figure 14:
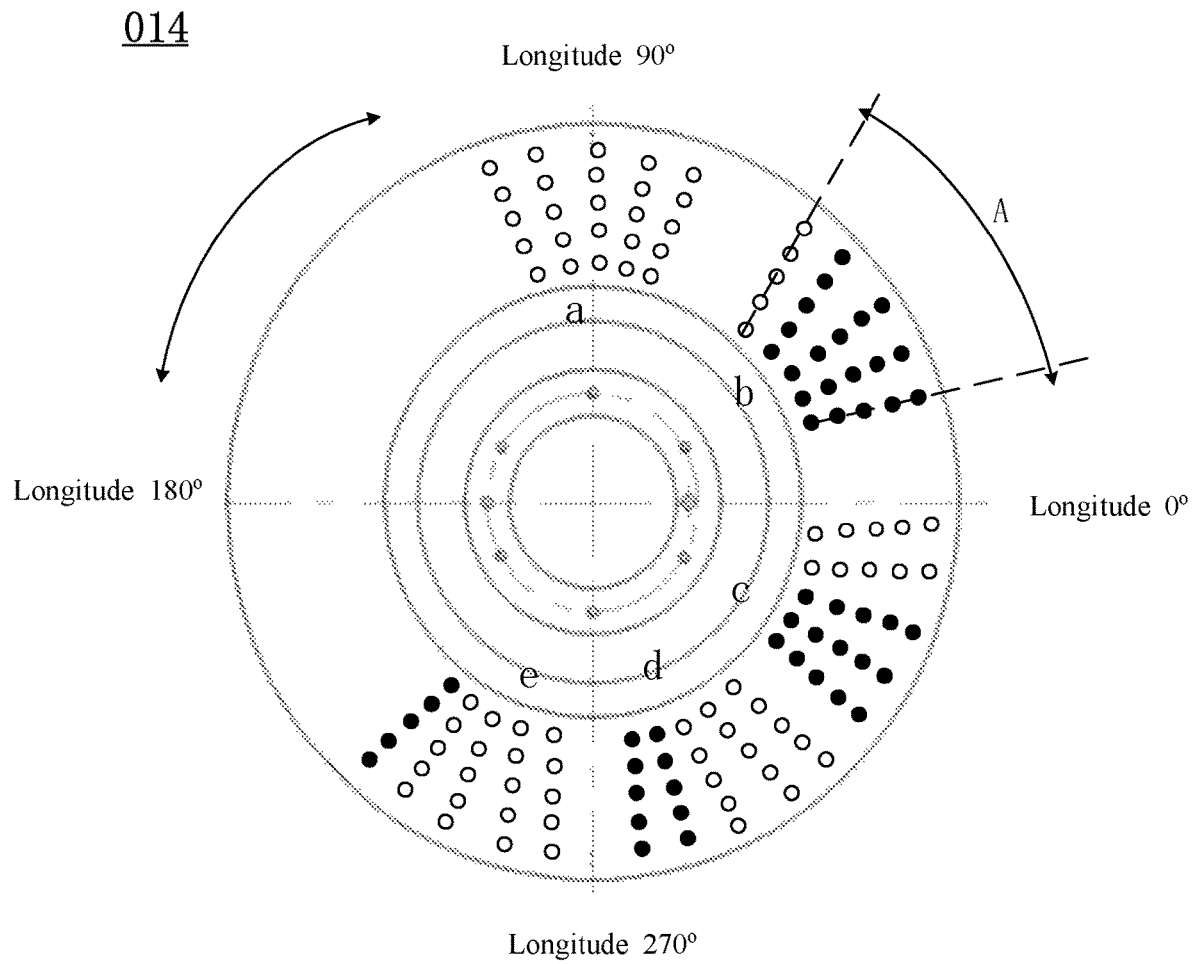
FIG. 14 is a schematic diagram of a switch body provided in an embodiment of the present disclosure.

For a radiotherapy device provided in the present disclosure, the radioactive source apparatus 01 further includes a switch body located between the source carrier 011 and the collimator 012. As shown in FIG. 14, the switch body 014 is provided with at least two sets of hole sites corresponding to the radioactive sources 04, where one set of the at least two sets of hole sites are all through holes, and each set of the rest sets of hole sites includes through holes and shielding sites 0122. For example, as shown in FIG. 14, the switch body 014 is provided with 5 sets of hole sites, namely sets a to e of hole sites, where hole sites of the set a are all through holes, hole sites of only a row of the set b are through holes while all other hole sites of the set b are shielding sites 0122, hole sites of two rows of the set c are through holes while all other hole sites of the set c are shielding sites 0122, hole sites of three rows of the set d are through holes while all other hole sites of the set d are shielding sites 0122, and hole sites of four rows of the set e are through holes while all other hole sites of the set e are shielding sites 0122. It should be noted that the shielding sites 0122 may be implemented by providing no holes on the switch body 014, or implemented by providing holes on the switch body 014 but filling the holes with tungsten rods to shield the radioactive sources 04.

For the radiotherapy device provided in the present disclosure, different hole sites are provided at different positions of the switch body 014, the number of holes for different hole sites is different, and then different hole sites of the switch body 014 may correspond to the radioactive sources 04 to selectively shield a part of the radioactive sources 04, and then adjust a dose at the common focus.

For a radiotherapy device provided in the present disclosure, the source carrier 011 and the collimator 012 are rotatable around a center axis of the radioactive source apparatus 01 circularly by 360° or reciprocally. The source carrier 011 and the collimator 012 rotating around the center axis of the radioactive source apparatus 01 reciprocally may be that the source carrier 011 and the collimator 012 rotating reciprocally within a range of 270 degrees. A reciprocal rotation angle thereof is not limited in the present disclosure. Only an example description is provided with the above description as an example.

For a radiotherapy device provided in the present disclosure, the source carrier 011 and/or the collimator 012 are/is movable along a preset trajectory. For example, as shown in FIG. 11, the source carrier 011 and/or the collimator 012 are/is movable along a center axis direction of the radioactive source apparatus 01. Alternatively, as shown in FIG. 12, the source carrier 011 and/or the collimator 012 are/is movable along a direction A. Specifically, the source carrier 011 may move along the center axis direction of the radioactive source apparatus 01, while the collimator 012 may be immovable; or the collimator 012 may move along the center axis direction of the radioactive source apparatus 01, while the source carrier 011 may be immovable; or, both the source carrier 011 and the collimator 012 may move along the center axis direction of the radioactive source apparatus 01. The source carrier 011 and/or the collimator 012 move/moves along the preset trajectory, which may realize switching on/off the source.

For a radiotherapy device provided in the present disclosure, the source carrier 011 and/or the collimator 012 are/is composed of a plurality of segments. For example, the radioactive source 04 may be located on one of the segments of the source carrier 011, or the segment may be movable along the center axis direction of the radioactive source apparatus 01. The collimator 012 may also be composed of a plurality of segments. The collimator 012 may include a plurality of collimating hole groups, and each of the collimating hole groups is correspondingly arranged on one segment, or one segment is provided with a plurality of collimating hole groups. Further alternatively, the collimator 012 may also be provided with source off sites, and a collimating hole group and a source off site may be arranged on one segment.

For a radiotherapy device provided in the present disclosure, the source carrier 011 may also be sheet-shaped, i.e., the source carrier 011 may be one segment among the plurality of segments. A specific shape of the source carrier 011 is not limited in the present disclosure.

During treatment, a tumor of a patient is required to be precisely located at the common focus 05 such that radioactive rays kill tumor cells. If the patient moves during treatment, then the radioactive rays will deviate, which not only goes against the treatment but also is harmful to the patient health. Because the common focus 05 of an existing radiotherapy device is located within a cavity of the radioactive source apparatus 01, it is impossible to monitor whether head of the patient moves during treatment. The radiotherapy device provided in the present disclosure can cause the common focus 05 to be located outside an end face of the radioactive source apparatus 01. For example, as shown in FIG. 8, FIG. 11, and FIG. 12, the common focus 05 is located outside the end face of the radioactive source apparatus 01, which contributes to observing and monitoring whether the patient moves during treatment.

For the radiotherapy device provided in the present disclosure, the radiotherapy device further includes an imaging apparatus 08, the imaging apparatus 08 is arranged on a side of the radioactive source apparatus 01 along the center axis direction of the radioactive source apparatus 01, and the common focus 05 is located within an imaging region of the imaging apparatus 08. That is, the tumor of the patient located within the imaging region may be imaged through the imaging apparatus 08, to determine whether the patient is displaced based on the image. The displacement is monitored precisely based on the image.

For the radiotherapy device of the present disclosure, the imaging apparatus 08 may be any one of an X-ray imaging apparatus, a CT imaging apparatus, an ultrasonic imaging apparatus, a DSA imaging apparatus, a MR imaging apparatus, or a PET imaging apparatus, or any combination thereof. For example, the imaging apparatus 08 is the X-ray imaging apparatus. For example, as shown in FIG. 8, FIG. 11, and FIG. 12, the imaging apparatus may include an X-ray bulb tube 081 and an X-ray flat panel 082, or may include two X-ray tubes 081 and two X-ray flat panels 082, and radiation beams emitted from the two X-ray tubes 081 intersect. Of course, the imaging apparatus 08 may also be a combination of any two or more different imaging apparatuses 08. For example, the imaging apparatus 08 may be a combination of the X-ray imaging apparatus and the DSA imaging apparatus. A specific setting of the imaging apparatus 08 is not limited in the present disclosure, and only an example description is provided with the above description as an example.

For example, the imaging apparatus 08 may include an imaging center point, and the common focus 05 overlaps with the imaging center point. For example, the imaging apparatus 08 includes two X-ray tubes 081 and two X-ray flat panels 082, each of the two X-ray flat panels 082 receives radiation beams emitted from the X-ray tubes 081 corresponding to the X-ray flat panels, and the radiation beams emitted from the two X-ray tubes 081 intersect at the common focus 05.

For the radiotherapy device provided in the present disclosure, the imaging apparatus 08 is rotatable along the center axis of the radioactive source apparatus 01. As shown in FIG. 8, FIG. 11, and FIG. 12, if the imaging apparatus 08 includes an X-ray bulb tube 081 and an X-ray flat panel 082, and the imaging apparatus 08 is immovable, then whether the patient moves in upward and downward directions as shown in FIG. 8, FIG. 11, and FIG. 12 cannot be determined based on the image. Therefore, if the imaging apparatus 08 rotates along the center axis of the radioactive source apparatus 01, the imaging apparatus can acquire images of the patient at different angles, thereby determining whether the patient moves at each angle.

The imaging apparatus 08 may rotate by installing a rotating unit on the imaging apparatus 08, e.g., by installing a gear ring, or by installing a slip ring drive. A rotating approach of the imaging apparatus 08 is not limited in the present disclosure.

For the radiotherapy device provided in the present disclosure, the imaging apparatus 08 is immovably connected to the radioactive source apparatus 01. For example, the imaging apparatus 08 is immovably connected to any one of the source carrier 011 or the collimator 012. For example, as shown in FIG. 8, the X-ray bulb tube 081 and the X-ray flat panel 082 may be immovably connected to the source carrier 011, such that the rotation of the source carrier 011 drives the imaging apparatus 08 to rotate, thereby avoiding separately providing a rotation driving apparatus for imaging. Of course, the imaging apparatus 08 may also be immovably connected to the switch body 014 or the collimator 012. This is not limited in the present disclosure.

For a radiotherapy device provided in the present disclosure, as shown in FIG. 8, FIG. 11, and FIG. 12, the radiotherapy device may further include a shielding apparatus 06, the shielding apparatus 06 is located on a side of the radioactive source apparatus 01, and the radiation beams emitted from the radioactive sources 04 are shielded by the shielding apparatus 06 after passing through the common focus 05. For example, as shown in FIG. 8, FIG. 11, and FIG. 12, the shielding apparatus 06 is located on a side of the common focus 05 of the radioactive source apparatus 01, and the radiation beams emitted from the radioactive sources 04 are shielded by the shielding apparatus 06 after passing through the common focus 05, thereby avoiding unnecessary radiation in the treatment chamber. For example, the shielding apparatus 06 is ring-shaped, and then the rays from the radioactive sources 04, when rotating around the center axis by one cycle, are all received by the shielding apparatus 06. Alternatively, the shielding apparatus 06 is a shielding block, which is rotatable along the center axis of the radioactive source apparatus 01, to synchronously rotate following the radioactive sources 04, and to receive the rays passing through the common focus 05. It should be noted that since a treatment couch 02 carries the patient to move, a channel is provided on the shielding apparatus 06 to facilitate the movement of the treatment couch 02.

For example, position settings of the shielding apparatus 06 and the imaging apparatus 08 are not limited in the present disclosure. For example, the imaging apparatus 08 may be separately immovably arranged, or may be arranged inside the shielding apparatus 06.

For the radiotherapy device provided in the present disclosure, as shown in FIG. 8, the radiotherapy device further includes a shielding door 07. The shielding door 07 can switch on or off a cavity of the radiotherapy device. For example, as shown in FIG. 8, the shielding door 07 may be arranged outside the cavity of the radioactive source apparatus 01, and can open or close the cavity of the radioactive source apparatus 01, which may be opened/closed upward and downward, or leftward and rightward. Therefore, during non-treatment time, the radiation beams may be shielded by the shielding door 07. Of course, the shielding door 07 may also be arranged between the imaging apparatus 08 and the shielding apparatus 06, or the shielding door 07 may be arranged outside the shielding door 07. A specific setting position of the shielding door 07 is not limited in the present disclosure, and only an example description is provided with FIG. 8 as an example.

For the radiotherapy device provided in the present disclosure, as shown in FIG. 7, an anti-sinking component (not shown in FIG. 7) is also provided between the collimator and the source carrier. Further, the radioactive source apparatus further includes a shielding body located outside the source carrier, and an anti-sinking component is also provided between the shielding body and the source carrier. For example, the anti-sinking component may be a bearing, thereby avoiding sagging at the other end when the collimator and the source carrier are driven to rotate at one end.

Figure 15:
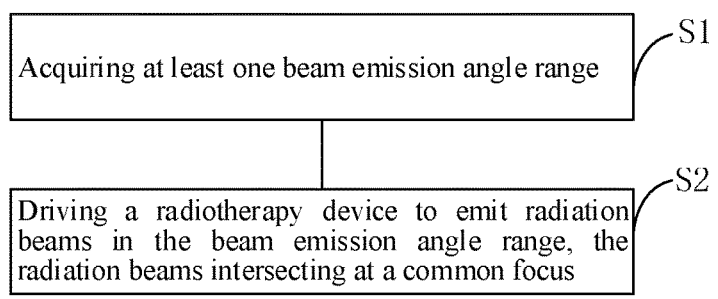
FIG. 15 is a schematic diagram of a control driving method provided in an embodiment of the present disclosure.

As shown in FIG. 15, a control driving method for a radiotherapy device provided in the present disclosure includes:

Step S1: acquiring at least one beam emission angle range.

Step S2: driving a radiotherapy device to emit radiation beams in the beam emission angle range, the radiation beams intersecting at a common focus.

Figure 16:
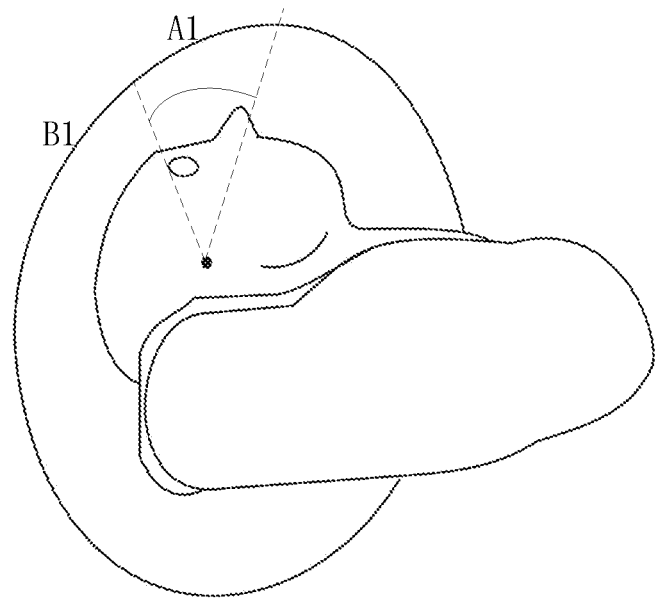
FIG. 16 is a schematic diagram of a radiotherapy provided in an embodiment of the present disclosure.

It should be noted that since a driving apparatus in the radiotherapy device is generally provided with a preset zero position, a driving angle range may be determined for driving with reference to the zero position during radiotherapy. In the present disclosure, the beam emission angle range may be an angle range that is required for a radiotherapy device to emit radiation beams for irradiation treatment and is included in a corresponding treatment plan formulated by a therapist based on a tumor image of a patient, and the angle range is a driving angle range of the driving apparatus. For example, as shown in FIG. 16, in the corresponding treatment plan formulated by the therapist based on the tumor image of the patient, the radiotherapy device performs irradiation treatment in a region B1 and does not perform irradiation treatment in a region A1 (the region A1 is an irradiated region including two eyes to prevent the rays from damaging optic nerves). Then, the beam emission angle range is a driving angle range of the driving apparatus driving the radioactive sources to irradiate the region B1, and a protection angle range is a driving angle range of the driving apparatus driving the radioactive sources to avoid irradiating the region A1. During radiotherapy, rotational irradiation is only required within the driving angle range of irradiation in the region B1, thereby avoiding irradiating the eyes and damaging the sensitive tissues. For example, the driving angle range is a rotation angle of a motor. Further, in the present disclosure, if the radiotherapy device rotates by more than 360 degrees, the driving angle range also exceeds 360 degrees. Alternatively, if the radiotherapy device rotates by more than 360 degrees, then the number of rotation cycles and driving angle ranges corresponding to different numbers of rotation cycles are calibrated.

Of course, during radiotherapy, rotational irradiation may also be performed on both of the region A1 and the region B1, and then the beam emission angle range is the driving angle range for irradiation in the region A1 and the region B1, e.g., 360 degrees. In this case, a dose received by the sensitive tissues, e.g., the optic nerves, may be reduced by reducing the irradiation duration, thereby protecting the sensitive tissues and organs.

For a control driving method provided in the present disclosure, a radiotherapy device includes a plurality of radioactive sources, and radiation positions of the plurality of radioactive sources are within a preset angle range in a longitude direction. The control driving method includes: acquiring at least one beam emission angle range, and driving the radiotherapy device to emit radiation beams in the beam emission angle range, the radiation beams intersecting at a common focus, thereby protecting the sensitive tissues and organs, e.g., eyes, from additional damages during the treatment of a head tumor.

Figure 17:
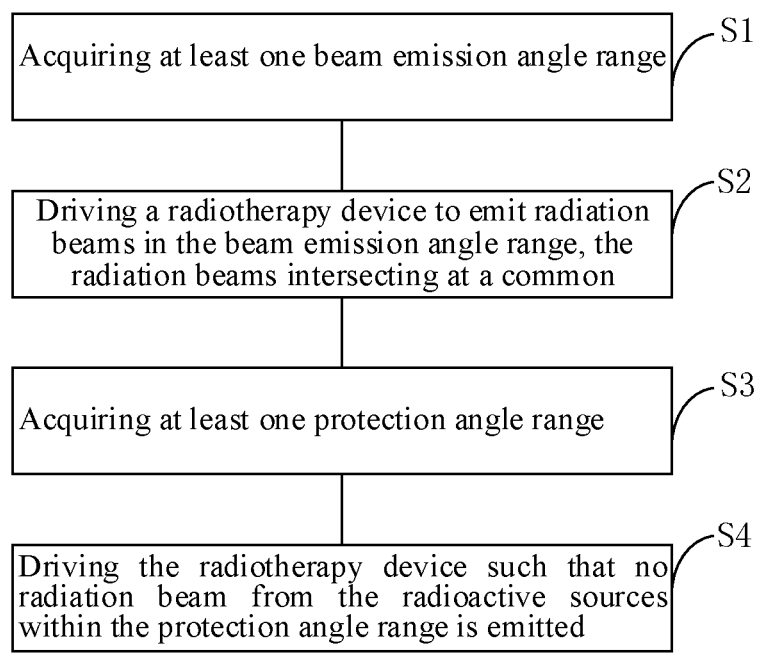
FIG. 17 is a schematic diagram of another control driving method provided in an embodiment of the present disclosure.

As shown in FIG. 17, a control driving method provided in the present disclosure further includes:

Step S3: acquiring at least one protection angle range. The at least one protection angle range is less than 360 degrees.

Figure 18:
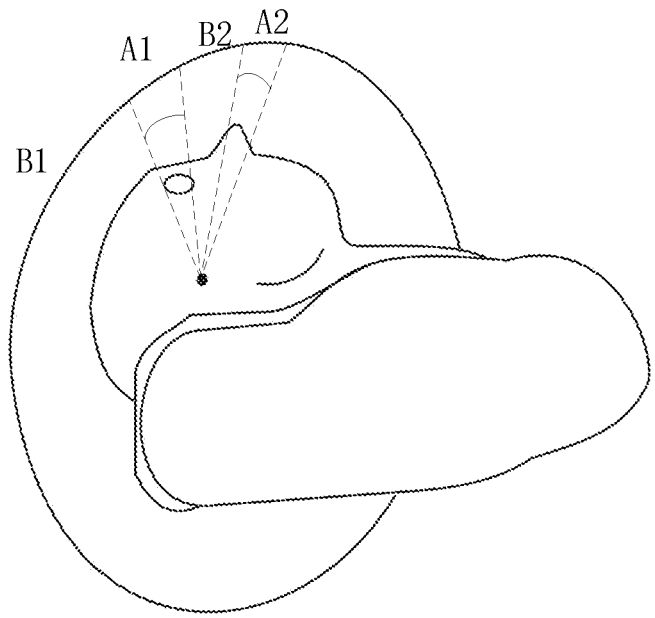
FIG. 18 is a schematic diagram of another radiotherapy provided in an embodiment of the present disclosure.

As shown in FIG. 18, the radiotherapy device performs irradiation treatment in a region B1 and a region B2, and does not perform irradiation treatment in a region A1 and a region A2 (the region A1 and the region A2 correspond to an eye region to prevent the rays from damaging the optic nerves). Then, the beam emission angle range is a driving angle range of the driving apparatus driving the radioactive sources to irradiate the region B1 and the region B2, and a protection angle range is a driving angle range of the driving apparatus driving the radioactive sources to avoid irradiating the region A1 and the region A2.

Step S4: driving the radiotherapy device such that no radiation beam from the radioactive sources within the protection angle range is emitted.

For a control driving method provided in the present disclosure, a radiotherapy device includes a plurality of radioactive sources, and radiation positions of the plurality of radioactive sources are within a preset angle range in a longitude direction. The control driving method includes: acquiring at least one beam emission angle range and at least one protection angle range, and driving the radiotherapy device to emit radiation beams in the beam emission angle range, the radiation beams intersecting at a common focus, such that no radiation beam from the radioactive sources within the protection angle range is emitted, thereby protecting the sensitive tissues and organs, e.g., eyes, from additional damages during the treatment of a head tumor.

For example, at least one of the at least one beam emission angle range is adjacent to at least one of the at least one protection angle range. As shown in FIG. 18, irradiation treatment is performed in the regions B1 and B2, and no irradiation treatment is performed in the regions A1 and A2. Since the region B1 is adjacent to the region A1, a beam emission angle range corresponding to the region B1 is adjacent to a protection angle range corresponding to the region A1.

The control driving method provided in the present disclosure includes: acquiring a plurality of beam emission angle ranges, and the radiotherapy device operates at different speeds within at least two of the beam emission angle ranges. For example, referring to FIG. 18, irradiation treatment is performed in the regions B1 and B2, and then the beam emission angle range corresponding to the region B1 and a beam emission angle range corresponding to the region B2 are acquired. The radiotherapy device operates at a speed of V1 in the beam emission angle range corresponding to the region B1, and at a speed of V2 in the beam emission angle range corresponding to the region B2, V1/V2, such that speed can be controlled to adjust the irradiation duration at different positions, and then adjust the dose at the focus.

For example, as show in FIG. 16, during radiotherapy, rotational irradiation is performed in both of the corresponding regions A1 and B1, and then the beam emission angle range is the driving angle range for irradiation in the region A1 and the region B1. In this case, the speed may be V1 in the beam emission angle range corresponding to the region B1, and V2 in the beam emission angle range corresponding to the region A1, V1<V2. That is, the speed in the region A1 is greater than the speed in the region B1, thereby reducing the dose received by the sensitive tissues within the region A1, to protect the sensitive tissues and organs.

It should be noted that the driving angle range in the present disclosure is the rotation angle of the motor, and the driving angle range also exceeds 360 degrees. For example, if the motor exceeds 360 degrees, then the number of rotation cycles and driving angle ranges corresponding to different numbers of rotation cycles are calibrated. The radiotherapy device operates at different speeds within at least two of the beam emission angle ranges, and may be driven at different driving speeds in a same corresponding irradiated region at different numbers of rotation cycles. For example, a planned treatment duration of radiotherapy is 2 minutes, and it takes 1 minute for the motor to be driven and rotate by one cycle. As shown in FIG. 18, a driving speed for irradiation in the region B1 is V1 in the beam emission angle range in a first cycle, and a driving speed for irradiation in the region B1 is V2 in the beam emission angle range in a second circle, V1/V2.

For the control driving method provided in the present disclosure, for example, as shown above, the two beam emission angle ranges corresponding to different speeds are adjacent.

For the control driving method provided in the present disclosure, the radiotherapy device is driven to reciprocate within the beam emission angle range. For example, if only one beam emission angle range is acquired, the radiotherapy device may reciprocate within the beam emission angle range to increase the dose received by the tumor. Of course, if a plurality of beam emission angle ranges is acquired, the radiotherapy device may also reciprocate within the beam emission angle ranges to increase the dose received by the tumor.

For the control driving method provided in the present disclosure, shielding sites may be provided on a shielding body. Then, step S4 in FIG. 17 may specifically include: driving the radiotherapy device such that the radiation beams emitted from the plurality of radioactive sources are shielded by the collimator. For example, the source carrier and the collimator may be driven to be misaligned, such that the radioactive sources on the source carrier are shielded by a gap between the collimating holes on the collimator. The source carrier is required to be misaligned with the collimator only by rotating a small angle, thereby realizing fast switching on/off the source; or the source carrier and the collimator may be driven to be misaligned, such that the radioactive sources on the source carrier are shielded by the shielding sites of the collimator.

Figure 19:
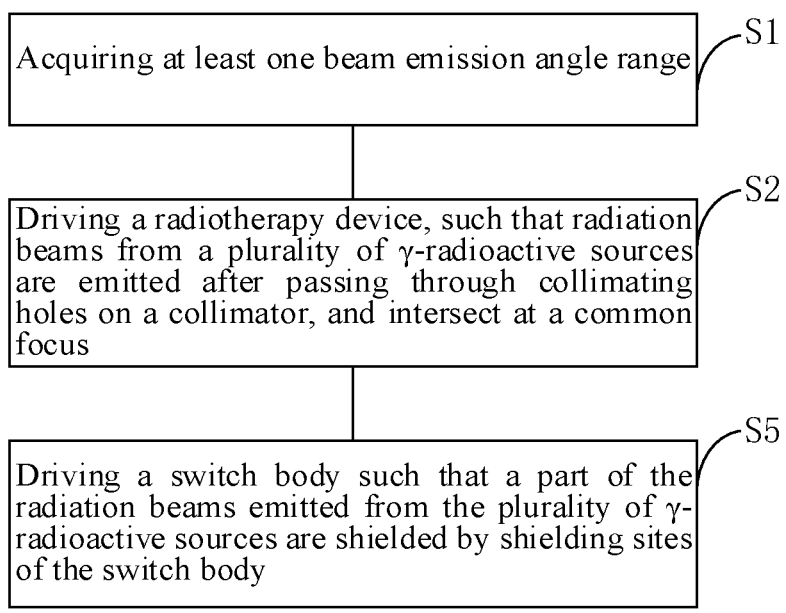
FIG. 19 is a schematic diagram of still another control driving method provided in an embodiment of the present disclosure.

For the control driving method provided in the present disclosure, the radiotherapy device further includes a switch body. Based on the method shown in FIG. 15, as shown in FIG. 19, the control driving method further includes:

Step S5: driving a switch body such that a part of the radiation beams emitted from a plurality of γ-radioactive sources are shielded by shielding sites of the switch body.

Of course, the control driving method as shown in FIG. 17 may also include step S5. FIG. 19 only takes the control driving method shown in FIG. 15 as an example.

The switch body is shown in FIG. 14. The switch body is driven, such that a part of the radiation beams emitted from the plurality of γ-radioactive sources are shielded by the shielding sites of the switch body, i.e., a part of the radiation beams from the radioactive sources may be shielded by the shielding sites of the switch body, thereby achieving the purpose of adjusting the dose.

For the control driving method provided in the present disclosure, a space between two adjacent collimating holes in a same collimating hole group is greater than a size of the radioactive source in the longitude direction. Then, step S4 as shown in FIG. 17 specifically includes: driving the radiotherapy device such that the plurality of radioactive sources is misaligned with the collimating holes, where a part of the radiation beams emitted from the radioactive sources are shielded by edge regions of the collimating hole group, and the rest of the radiation beams emitted from the radioactive sources are shielded by space regions between the collimating holes. For example, the source carrier and the collimator may be driven to be misaligned, such that the radioactive sources on the source carrier are shielded by a gap between the collimating holes on the collimator. The source carrier is required to be misaligned with the collimator only by rotating a small angle, thereby realizing fast switching on/off the source.

Figure 20:
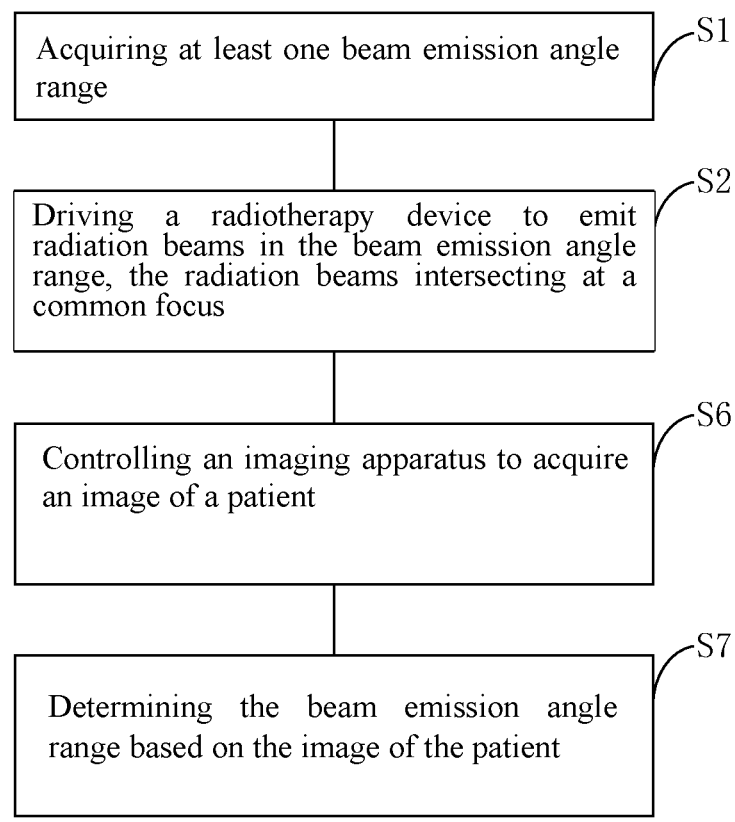
FIG. 20 is a schematic diagram of yet another control driving method provided in an embodiment of the present disclosure.

For example, for the radiotherapy device as shown in FIG. 8, FIG. 11, and FIG. 12, the common focus is located outside the end face of the radioactive source apparatus. The radiotherapy device further includes an imaging apparatus, and the common focus is located within an imaging region of the imaging apparatus. As shown in FIG. 20, the control driving method further includes:

Step S6: controlling an imaging apparatus to acquire an image of a patient.

Step S7: determining the beam emission angle range based on the image of the patient.

It should be noted that the beam emission angle range in step S1 may be a beam emission angle range determined by a therapist based on the image of the patient before radiotherapy, and may be determined or adjusted based on the acquired image during treatment.

Figure 21:
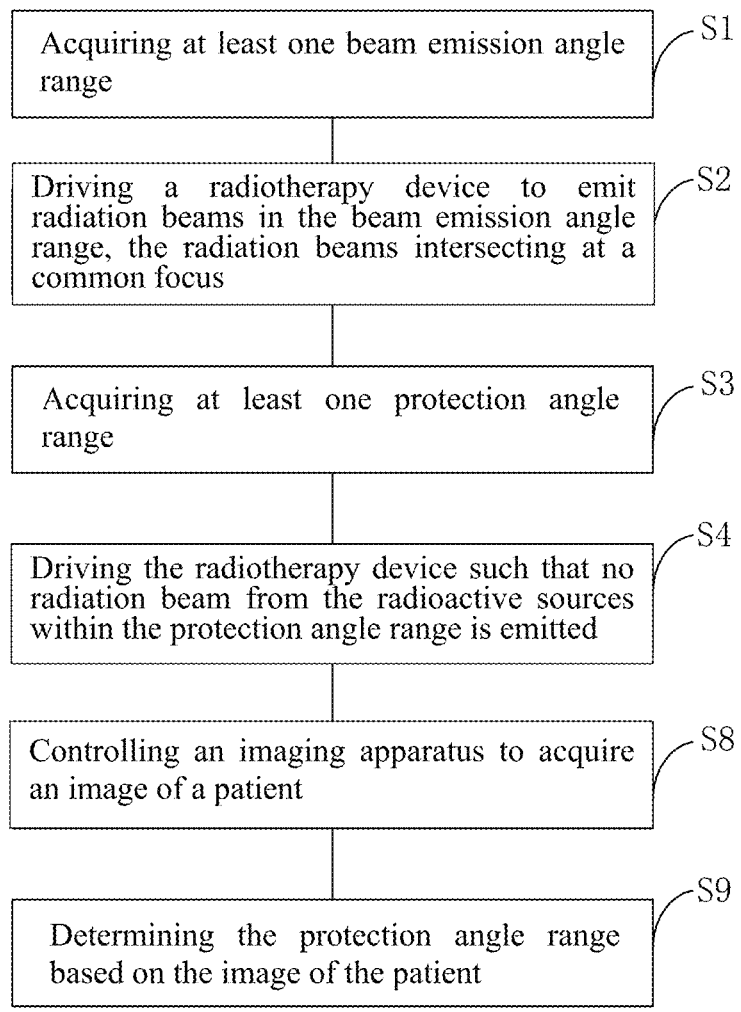
FIG. 21 is a schematic diagram of yet still another control driving method provided in an embodiment of the present disclosure.

For example, the radiotherapy device as shown in FIG. 8, FIG. 11, and FIG. 12 further includes an imaging apparatus, and the common focus is located within an imaging region of the imaging apparatus. As shown in FIG. 21, the control driving method further includes:

Step S8: controlling the imaging apparatus to acquire the image of the patient.

Step S9: determining the protection angle range based on the image of the patient.

Likewise, the protection angle range in step S3 may be a protection angle range determined by the therapist based on the image of the patient before radiotherapy, and may be determined or adjusted based on the acquired image during treatment.

It should be noted that, for the control driving method provided in the present disclosure, the sequence of the above steps is not limited in the present disclosure, and only an example description is provided with the figures as an example in the present disclosure.

The present disclosure further provides a control driving device corresponding to the control driving method for the radiotherapy device. The control driving method may be referred to for a part of description of the driving apparatus. The description will not be repeated below.

Figure 22:
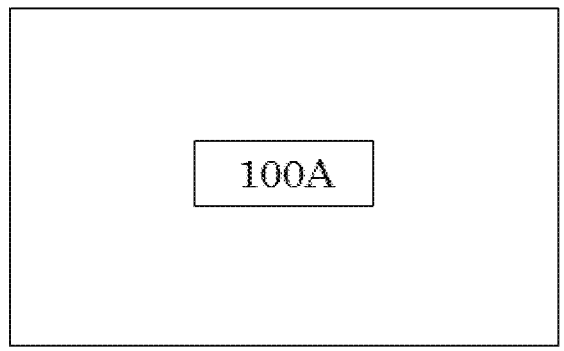
FIG. 22 is a schematic diagram of a control driving device provided in an embodiment of the present disclosure.

The present disclosure provides a radiotherapy system, including: the radiotherapy device provided in the present disclosure, and the control driving device provided in the present disclosure. The control driving device 100 as shown in FIG. 22 includes a processor 100A configured to implement any one of the control driving methods provided in the present disclosure.

It should be noted that the term "and/or" in embodiments of the present disclosure is merely an association relationship describing associated objects, and means that there may be three relationships. For example, A and/or B may mean three circumstances: only A exists, both A and B exist, and only B exists. In addition, the character "/" herein generally means that there is an "or" relationship between associated objects therebefore and thereafter.

The above description only provides alternative embodiments of the present disclosure, and is not intended to limit the present disclosure. Any modification, equivalent replacement, improvement, and the like made within the spirit and principles of the present disclosure should be included within the scope of protection of the present disclosure.

What is claimed is:

1. A radiotherapy device, comprising:
    a radioactive source apparatus, the radioactive source apparatus comprising a source carrier and a collimator,
    the source carrier being provided with a plurality of radioactive sources thereon, an angle of the plurality of radioactive sources in a longitude direction being within a preset angle range;
    the collimator being provided with a plurality of collimating hole groups thereon, an angle of each of the plurality of collimating hole groups in the longitude direction being within a preset angle range; and
    each of the plurality of collimating hole groups comprising a plurality of collimating holes, and radiation beams emitted from the plurality of radioactive sources intersecting at a common focus after passing through the plurality of collimating holes of the plurality of collimating hole groups, wherein the common focus is located outside an end surface of the radioactive source apparatus,
    the radiotherapy device further comprising an imaging apparatus, wherein the imaging apparatus is arranged on a side of the radioactive source apparatus along a center axis direction of the radioactive source apparatus, and the common focus is located within an imaging region of the imaging apparatus.

2. The radiotherapy device according to claim 1, wherein the source carrier and the collimator are rotatable around a center axis of the radioactive source apparatus circularly by 360° or reciprocally.

3. The radiotherapy device according to claim 1, wherein the source carrier and/or the collimator are movable along a preset trajectory.

4. The radiotherapy device according to claim 1, wherein the imaging apparatus comprises an imaging center point, and the common focus overlaps with the imaging center point.

5. The radiotherapy device apparatus according to claim 1, wherein the imaging apparatus comprises two X-ray tubes and two X-ray flat panels, each of the two X-ray flat panels receives a radiation beam emitted from one of the two X-ray tubes, and radiation beams emitted from the two X-ray tubes intersect at the common focus.

6. The radiotherapy device according to claim 1, wherein the imaging apparatus is immovably connected to the radioactive source apparatus.

7. The radiotherapy device according to claim 6, wherein the imaging apparatus is immovably connected to any one of the source carrier or the collimator.

8. The radiotherapy device according to claim 1, further comprising: a shielding apparatus, the shielding apparatus is located on a side of the radioactive source apparatus, and the radiation beams emitted from the plurality of radioactive sources are shielded by the shielding apparatus after passing through the common focus.

9. A radiotherapy system, comprising:
    a radiotherapy device, the radiotherapy device comprising a radioactive source apparatus, the radioactive source apparatus further comprising a source carrier and a collimator, wherein
    the source carrier is provided with a plurality of radioactive sources thereon, an angle of the plurality of radioactive sources in a longitude direction is within a preset angle range;
    the collimator is provided with a plurality of collimating hole groups thereon, an angle of each of the plurality of collimating hole groups in the longitude direction is within a preset angle range;
    each of the plurality of collimating hole groups comprises a plurality of collimating holes, radiation beams emitted from the plurality of radioactive sources intersecting at a common focus after passing through the plurality of collimating holes of the plurality of collimating hole groups, and the common focus is located outside an end surface of the radioactive source apparatus; and
    the radiotherapy system further comprises a control driving device, the control driving device comprises a processor, and the processor is programmed to:
    acquire at least one beam emission angle range; and
    drive the radiotherapy device to emit radiation beams in the at least one beam emission angle range, the radiation beams intersecting at the common focus.

10. The radiotherapy system according to claim 9, wherein the processor is further programmed to:
    acquire at least one protection angle range; and
    drive the radiotherapy device, such that no radiation beams within the at least one protection angle range are emitted from the plurality of radioactive sources.

11. The radiotherapy system according to claim 10, wherein the at least one protection angle range is less than 360°.

12. A radiotherapy device, comprising:
    a radioactive source apparatus, the radioactive source apparatus comprising a source carrier and a collimator,
    the source carrier being provided with a plurality of radioactive sources thereon, an angle of the plurality of radioactive sources in a longitude direction being within a preset angle range;
    the collimator being provided with a plurality of collimating hole groups thereon, an angle of each of the plurality of collimating hole groups in the longitude direction being within a preset angle range; and
    each of the plurality of collimating hole groups comprising a plurality of collimating holes, and radiation beams emitted from the plurality of radioactive sources intersecting at a common focus after passing through the plurality of collimating holes of the plurality of collimating hole groups, and wherein the radioactive source apparatus further comprises a switch body, the switch body is located between the source carrier and the collimator, and the switch body is provided with at least two sets of hole sites corresponding to the plurality of radioactive sources, wherein one set of the at least two sets of hole sites are all through holes, and each set of the rest sets of the at least two sets of hole sites comprises through holes and shielding sites.

13. The radiotherapy device according to claim 12, wherein the source carrier and the collimator are rotatable around a center axis of the radioactive source apparatus circularly by 360° or reciprocally.

14. The radiotherapy device according to claim 12, wherein the source carrier and/or the collimator are movable along a preset trajectory.

15. The radiotherapy device according to claim 12, wherein the common focus is located outside an end surface of the radioactive source apparatus.

16. The radiotherapy device according to claim 15, further comprising: an imaging apparatus, the imaging apparatus is arranged on a side of the radioactive source apparatus along a center axis direction of the radioactive source apparatus, and the common focus is located within an imaging region of the imaging apparatus.

17. The radiotherapy device according to claim 16, wherein the imaging apparatus comprises an imaging center point, and the common focus overlaps with the imaging center point.

18. The radiotherapy device according to claim 16, wherein the imaging apparatus is immovably connected to the radioactive source apparatus.

19. The radiotherapy device according to claim 18, wherein the imaging apparatus is immovably connected to any one of the source carrier or the collimator.

\* \* \* \* \*